United States Patent [19]
Arndt

[11] Patent Number: 5,737,071
[45] Date of Patent: Apr. 7, 1998

[54] METHOD AND APPARATUS FOR ENHANCING LIVE-SCAN FINGERPRINT READER IMAGES

[75] Inventor: Douglas C. Arndt, Ventura, Calif.

[73] Assignee: Identicator Corporation, San Bruno, Calif.

[21] Appl. No.: 689,925

[22] Filed: Aug. 16, 1996

[51] Int. Cl.⁶ .................................................. G06K 9/00
[52] U.S. Cl. ..................... 356/71; 427/1; 118/31.5; 382/124; 382/125
[58] Field of Search .................... 427/1; 118/31.5; 356/71; 382/115, 116, 124, 125, 127

[56] References Cited

U.S. PATENT DOCUMENTS

| | | | |
|---|---|---|---|
| 4,053,228 | 10/1977 | Schiller | 356/71 |
| 4,262,623 | 4/1981 | Smith, III et al. | 118/31.5 |
| 4,532,508 | 7/1985 | Ruell | 382/4 |
| 4,728,186 | 3/1988 | Eguchi et al. | 356/71 |
| 5,088,817 | 2/1992 | Igaki et al. | 356/71 |
| 5,189,482 | 2/1993 | Yang | 356/73 |
| 5,395,444 | 3/1995 | Arndt et al. | 118/31.5 |
| 5,448,649 | 9/1995 | Chen et al. | 356/71 |
| 5,621,516 | 4/1997 | Shinzaki et al. | 356/71 |

FOREIGN PATENT DOCUMENTS

| | | | |
|---|---|---|---|
| 304092 | 2/1989 | European Pat. Off. | 427/1 |
| 5469300 | 7/1979 | Japan | 118/31.5 |
| 2276732 | 10/1994 | United Kingdom | 427/1 |
| 86006266 | 11/1986 | WIPO | 427/1 |
| 9608786 | 3/1996 | WIPO | |

*Primary Examiner*—Erma Cameron
*Attorney, Agent, or Firm*—Harold L. Jackson

[57] ABSTRACT

A method and apparatus for improving the optical boundary between a person's fingerprint ridges and the surface platen of a live-scan-imaging apparatus includes providing an absorbent pad containing chemicals selected from the non-volatile oils, oil amides, fatty alcohols and fatty acid esters, placing the person's finger to be scanned on the surface of the absorbent pads to coat the fingerprint ridges and subsequently placing the person's finger with the coated fingerprint ridges on the platen of the imaging apparatus to provide a high contrast between the ridges and valleys of the fingerprint area.

11 Claims, 3 Drawing Sheets

METHOD AND APPARATUS FOR ENHANCING LIVE-SCAN FINGERPRINT READER IMAGES

FIELD OF THE INVENTION

The present invention relates to a method and apparatus for enhancing fingerprint images recorded by live-scan-electro-optical imaging equipment and more particularly to such a method and apparatus which provides a coating of a liquid composition on the ridges of the finger tips prior to the placement thereof on the recording surface of the equipment.

BACKGROUND OF THE INVENTION

Live-scan-electro-optical-imaging apparatus (hereinafter "live-scan-imaging apparatus" or "live-scan-fingerprint readers") captures or, "reads" fingerprint ridge detail directly from the finger. The process, commonly referred to as "live-scanning", can immediately process a finger print with the aid of a computer.

Positive identification of an individual obtained through fingerprints is the only widely accepted method of personal identification. To provide accurate identification fingerprint images must be as sharp as possible with high contrast between the ridge lines (crests) and the recesses (valleys) therein. Furthermore, fingerprint images should not contain distortions or false details such as discontinuities in the ridge lines. Such aberrations are referred to in the art of fingerprinting as "artifacts". The term "fingerprints" will be used in this application in a generic sense to also encompass ridge patterns taken from an individual's thumbs, hands, toes, and feet.

FIG. 1 schematically illustrates a typical prior art live-scan-imaging apparatus. The apparatus includes a prism 16 with a thin elastomeric membrane 12 on the normally reflecting surface thereof. The prism and the membrane 12 form the platen or window. The elastomeric membrane or coating allows the surface 13 to more readily accommodate ridge line discontinuities as will be explained. It should be noted that such coatings are not used in all live-scan-fingerprint readers and the present invention accommodates ridge line discontinuities thereby eliminating or reducing the need for such coatings.

When a finger or thumb 10 is pressed or rolled upon the surface 13 of the prism 16, the light directed thereto, from a source 14 via a lens 15, is internally reflected to an electronic imaging device 17 such as a CCD camera. The fingerprint image is obtained by utilizing the change in boundary conditions which occur on the platen surface where the finger is placed. Incident light rays are arranged to strike the surface of the platen such that the valleys cause the light to be totally internally reflected. This principle is known as Frustrated Total Internal Reflection and is based upon Snell's Law, i.e., incident light on an interface going from a higher refractive index to a lower refractive index (e.g. glass to air) will be totally reflected if the incident angle is large enough. Only the ridges of a fingerprint contact the platen, while air is disposed within the valleys. Thus, light incident at the proper angle under the valleys is reflected while light striking the ridges will be absorbed, as is illustrated in FIG. 2 where the numerals 18 and 19 designate the ridges and valley's, respectively. This reflection, frustrated along the fingerprint ridges, results in a high-contrast pattern, e.g., black and white.

As shown in FIG. 3, the surface of a typical fingerprint ridge is not flat and mirror-like, but textured. This ridge line topography can and does prevent a uniform contact with the window or platen surface when the finger is dry or calloused, making it very difficult to obtain clear fingerprint images. Compare the point contact 20 of the ridge 19 in FIG. 3 versus the substantial ridge contact with the platen shown in FIG. 2. The uneven contact of a ridge line with the platen produces its own delta of refractive indices due to the pockets of air present between portions of the ridge and the window. In the case of dry fingers, ridge lines may appear spotty, discontinuous, and faint. It has been particularly difficult to obtain readable images of fingerprints where the fingertips are worn and dry. Applying heavy contact pressure with the fingers helps somewhat to flatten the ridges and improve uniform contact with the window, but the added pressure tends to push ridge lines together eliminating the valleys therebetween, thereby distorting the fingerprint pattern. Moreover, pressure gradients within the fingerprint produce corresponding gradients in ridge line contrast and continuity.

To obtain faithful reproductions of fingerprint minutiae (combination of ridges and valleys), a number of ridge line enhancement methods have been devised. The angles of incidence and refraction at a glass/air boundary can be both reflected and refracted by a prism to minimize the refractive indices attendant to ridge line irregularities. Image enhancement may also be achieved by using appropriate computer software. A common approach is to coat the optical window with an elastomeric coating or pliant material (e.g., coating 12 of FIG. 1) thus allowing the surface to conform to some extent to the ridge line discontinuities and fill in air spaces. While this technique is helpful in creating better optical boundary conditions in many cases, it is of little help where the fingers are dry and/or the ridges are worn down.

An atomizer capable of supplying a fine mist to moisten the skin has also been used to displace air contained within the ridge line topography. However, this technique is difficult to control and consequently the valleys within the fingerprint can get filled in with the fluid, which in turn reduces image clarity. In an attempt to coat the ridges more evenly without filling in the valleys, finger gel tackifiers, such as those used by bank tellers, have also been tried. However, due to their poor penetration into the skin, the tackifying chemicals leave deposits on the optical window, which deposits create interference. Deposits left on the window absorb and scatter light, resulting in lower print contrast and blurred images. The build up of residues must be removed from the window surface in order to obtain clear fingerprint reproductions. Frequent cleaning of the window is both inconvenient and an added expense.

Because hand creams and lotions have good penetration into the skin, they have been used to soften dry fingers for the purpose of obtaining improved fingerprint images. However, the dispensing methods do not meter out consistent amounts of material, so it is easy to overcoat the fingers and greasy residues can build up on the platen. One must often wait lengthy periods of time for excess material on the skin to be absorbed or evaporate, which slows down the fingerprinting process. Another disadvantage with lotions is that they are not formulated specifically for the live-scan-imaging apparatus. Certain ingredients create unfavorable optical boundary conditions due to their characteristic reflection, absorption, and refraction of light, especially in the infrared and near infrared light region of the spectrum. Of the various hand lotions, Corn Huskers Lotion® has probably been used more frequently than other lotions because the formulation may be the least problematic in that it is non-greasy, colorless, and penetrates the skin rapidly. However, Corn Huskers Lotion® (water, glycerin, SD alcohol 40, sodium calcium alginate, oleyl sarcosine, methyl paraben, guar gum, triethanolamine, calcium sulfate, fumetic acid, and boric acid) does not provide a high degree of image enhancement in comparison to the liquids employed in the present invention. Corn Huskers is a trademark of Warner-Lambert.

Another factor that results in reduced image clarity is perspiration. For some individuals, fingerprinting can be particularly stressful, especially when it is associated with an arrest. In these circumstances, people tend to perspire profusely. Heavy perspiration may also be the symptom of a medical condition known as hydroporosity. FIG. 4 illustrates the many sweat glands 21, sweat ducts 22, and pores 24 found within a person's fingerprint area.

A number of methods have been devised to combat perspiration. These methods include the use of moisture-removing chemicals such as desiccant powders and evaporative alcohols, ketones, and ethers. These materials are typically difficult to apply uniformly and they often produce undesirable optical boundary conditions. To avoid negative light scattering properties, another method incorporates into the live-scan-imaging apparatus a mechanism that directs a steady stream of dry air to remove water-based moisture from the fingers. This is an added expense and it does nothing to address the problems previously discussed concerning fingerprint ridge discontinuities.

There is a need for a method and apparatus for applying an appropriate liquid coating to a person's fingers prior to the placement of the finger(s) on the optical window of a live-scan-imaging apparatus to overcome the above problems and improve the quality of the recorded fingerprint.

SUMMARY OF THE INVENTION

In accordance with the present invention, at least one finger of a person to be fingerprinted with a live-scan-imaging, apparatus is first quickly and accurately coated with a liquid composition capable of enhancing the resolution of a fingerprint ridge pattern. A liquid composition comprising one or more of the nonvolatile oils, fatty alcohols and fatty acid esters provides superior optical boundary conditions and is preferably precisely metered to the fingerprint ridges by a pad comprised of a substantially rigid, porous surface and an internal reservoir.

The features of the present invention, both in terms of the method and apparatus, will best be understood by references to the following description taken in conjunction with the accompanying drawings.

DESCRIPTION OF THE PREFERRED EMBODIMENT

Figure 1:
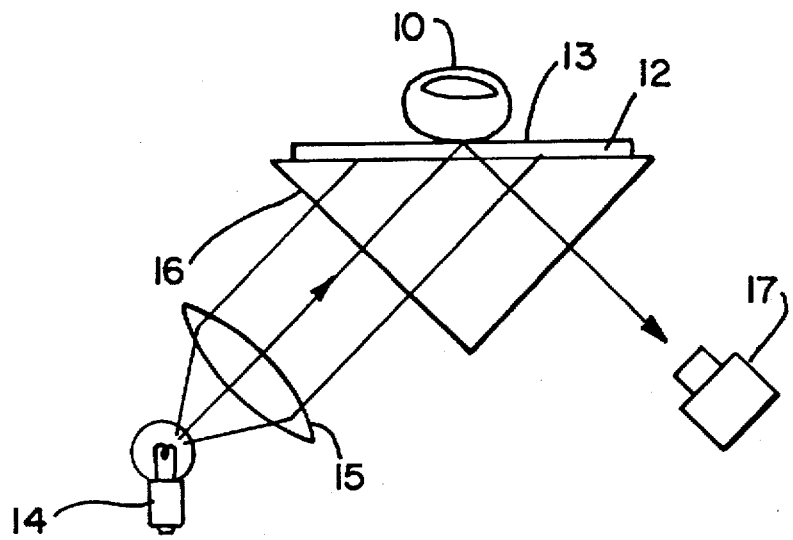
FIG. 1 is a diagrammatic view of a typical live-scan-imaging apparatus showing a finger 1 placed on top of an optical window or platen 12 which is coated with a compliant elastomeric material 13.
Figure 2:
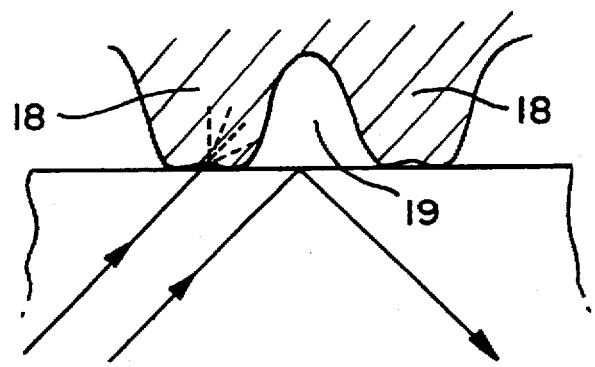
FIG. 2 is a side-elevational diagram showing light rays scattering off the boundary conditions created by a fingerprint ridge 18 and reflecting from the boundary conditions created by the air spaces within a fingerprint valley 19.
Figure 3:
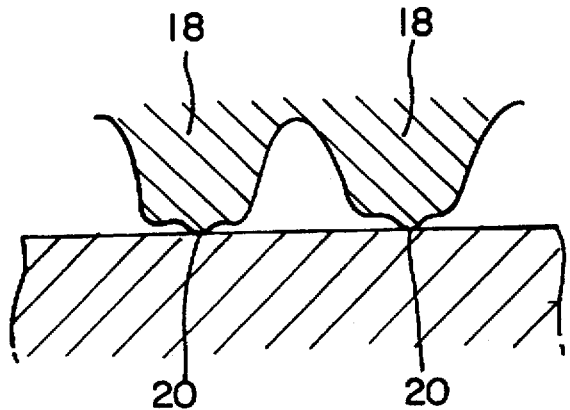
FIG. 3 is an illustration of the surface discontinuities 10 on the fingerprint ridge of a dry finger.
Figure 4:
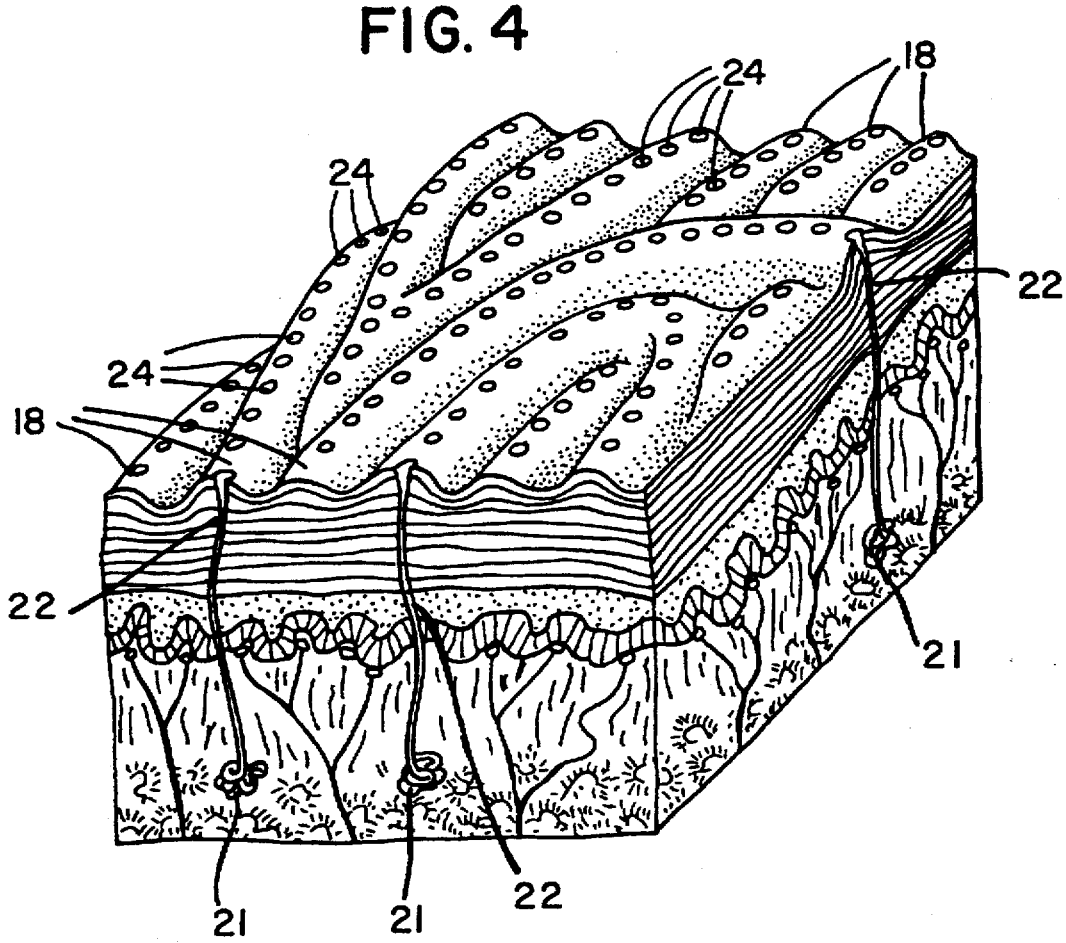
FIG. 4 is a cross-sectional view of a skin section underlying the fingerprint area showing sweat glands pores, etc.
Figure 5:
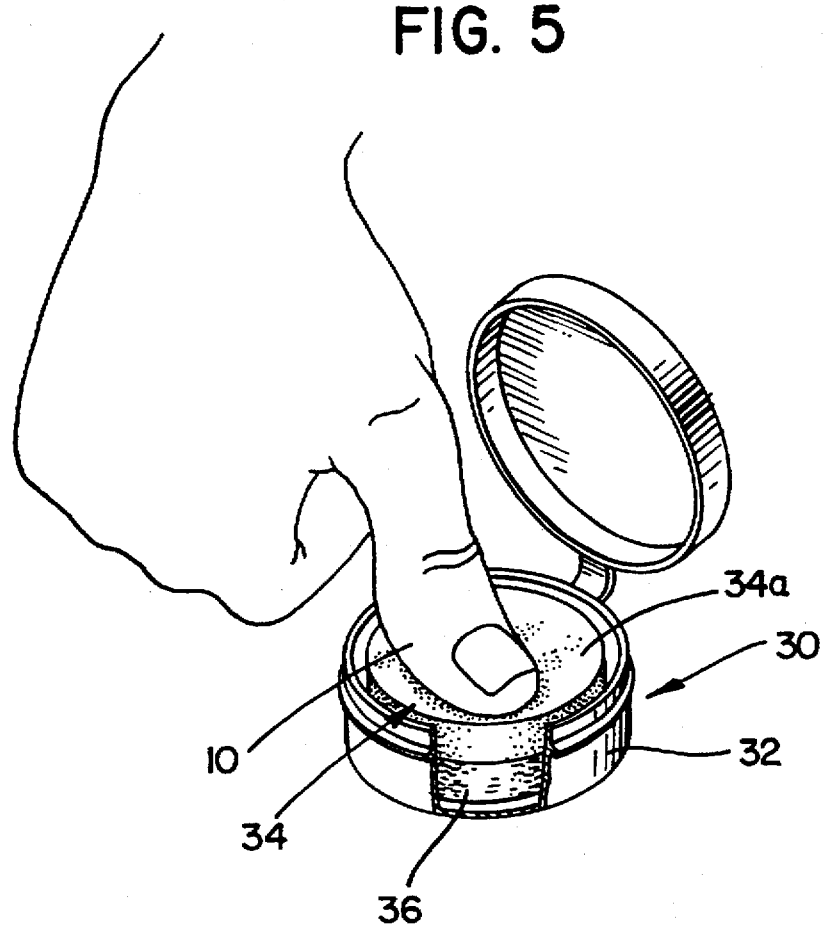
FIG. 5 is a perspective view of an absorbent pad arrangement for applying a liquid composition to the fingerprint area of a person's finger in accordance with the present invention.

Referring now to FIG. 5, it has been discovered that the best way to coat only the ridges of a fingerprint, with the liquid chemical composition of the invention (to be described), is to utilize a self-contained-metering/reservoir pad arrangement 30. The pad arrangement comprises an exterior or top microporous-metering member 34 that is substantially rigid and supplied with the coating liquid via an internal reservoir 36. The top surface of the pad 34 is designated 34a.

The top porous-metering member or pad 34 includes a top surface 34a through which the liquid is metered to the fingerprint area of the person's finger (illustrated as the thumb in FIG. 5). The metering pad 34 is preferably made of a suitable substantially rigid material, e.g., ceramic or plastic, having a pore volume of 10 to 50 percent (10–50%) and a pore diameter distribution within the range of about 0.10 to 10.0 microns. Preferably the mean pore diameter of the dispensing pad is within the range of about 0.75 to 1.2 microns and most preferably about 0.9 microns with a maximum pore diameter of about 0.12 microns. The metering pad 34 should be substantially rigid and noncompressible in response to the pressure of a fingertip placed thereon for coating purposes. The use of pads which are compressible, such as typical stamp pads, have a tendency to cause overcoating of the finger, i.e., filling in the valleys along with coating ridges. Such overcoating generally results in flooded images having poor resolution. Also, such typical stamp pads do not deliver a consistent amount of liquid to the finger because as the liquid is depleted, the concentration within the substrate decreases with less liquid being delivered to the finger.

A preferred substantially noncompressible-metering pad for use in the present invention utilizes a microporous ceramic with the following specification:

Density 2.1–2.2 grams/cm$^3$

Pore Volume 35 to 42 percent

Darcy permeability constant 0.07 to 0.08 darcy

Mean pore size 0.9 to 0.93 microns

Large pore size 5.9 microns

Figure 6:
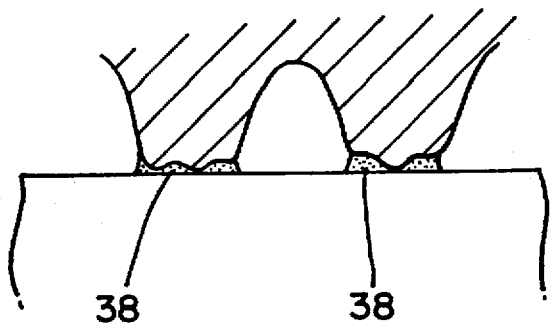
FIG. 6 depicts a fingerprint ridge as placed on an imaging apparatus window after it has been coated with the liquid chemical composition in accordance with the present invention.

When the liquid composition is metered through a porous material with such specifications, only the fine surface defining the fingerprint ridges are coated, as depicted in FIG. 6, creating optimum optical boundary conditions for high-clarity imaging and for minimizing the buildup of residue upon the window of the live-scan-imaging apparatus.

A reservoir pad 36 is used to supply the liquid to the porous-metering pad 34. The reservoir pad 36 may also be made of ceramic and as such can be molecularly bonded to the metering member 34 and the two pads may be manufactured as a composite ceramic with two distinct porosity layers. Alternatively, if both reservoir and metering pads are made of high-density polyethylene, they may be produced simultaneously as a composite structure having a molecular bond. The reservoir pad 36 may also be an open-cell foam (e.g. reticulated polyester) or an industrial grade felt. The choice of the reservoir material itself is only critical in that it must be chemically compatible with the liquid chemical composition 38 that is used. The reservoir pad 36 must be in intimate contact with the porous-metering pad 34 to ensure that capillary action takes place at the interface of the two pads. The pads may be bonded or secured together mechanically.

The porous reservoir pad 36 must have a pore volume and pore size greater than that of the metering pad to allow liquid to flow into the metering pad via capillary action. A useful range of pore volume of the reservoir pad is 40 to 80 percent. The capillary attraction within the material forming the metering pad 34 must be greater than that of the material forming the reservoir pad. Since a smaller pore diameter creates greater capillary pressure than a large pore diameter, liquid is drawn from the large pores into the small pores to the extent that the pressure differential exceeds the effect of gravity upon the weight, viscosity, and surface tension of the liquid. The flow of liquid to the finger will be consistent throughout the use of the pad until the liquid within the reservoir is depleted. This is a great advantage over the prior art stamp pads previously discussed. It should be noted that a dispensing pad arrangement similar to 30, utilizing a ceramic metering pad and a felt reservoir, has been used by the assignee of this application, Identicator Corporation, to dispense inkless fingerprinting reagents for the development of fingerprints on fingerprint cards, checks, etc. See U.S. Pat. No. 4,263,623.

A liquid chemical composition suitable for use in the present invention must meet certain requirements. First, it is desirable that a liquid composition, used with a free standing pad (e.g., pad 30 of FIG. 5) as contrasted with a hermetically sealed pad, have a reasonably long shelf-life. Thus, the liquid used in such pads (a) must have a very low evaporation rate, (b) should resist oxidation, (c) not readily become rancid, (d) not absorb gasses and moisture from the atmosphere, (e) not promote bacteriological growth, and (f) be nonphotochemically reactive and stable in ultraviolet light. There must also exist a chemical compatibility between the liquid and the raw materials from which the pad is constructed. Where the liquid is impregnated into a porous pad or substrate, which is hermetically sealed, i.e, via a plastic membrane until use, some of the above requirements are not applicable. Since the liquid is applied to the skin of a finger, it must not create a risk to one's health by means of subcutaneous absorption. It should be nonirritating and noncorrosive to the tissues of the finger. It must not produce adverse toxilogical effects or allergic reactions. The liquid must also be substantially insoluble in or immiscible with water, so that it is able to resist being flushed around the fingerprint ridges and into the valleys by perspiration. The liquid must soften and wet the surface of dry skin to make the dry ridge lines more conformable to the platen of a live-scan-fingerprint reader.

Since the liquid is used to optically enhance images reproduced by the reader, it must be compatible with the optical window upon which the finger is placed, and it should preferably create optical boundary conditions identical to or close to those of the optical surface to obtain maximum effect. The optical window is often provided with a thin coating of an elastomer such as silicone as discussed previously. The enhancement liquid and any solvent used to clean up its residues should be chemically inert in relationship to the coating to prevent an degradation thereof.

The liquid composition of this invention largely alleviates the need for a pliant coating on the optical window or platen because the composition renders the fingerprint ridges supple and thus minimizes the optical discontinuity between the ridges and the glass window. The composition eliminates or greatly reduces any need for desiccants, moisture removing solvents, and dry air streams because it displaces moisture on the finger. The composition further minimizes the need for special electro-optical enhancement techniques because it inherently provides optimum optical boundary conditions by matching the index of refraction of contact areas to that of the window.

It has been found that liquid compositions selected from one or more of the nonvolatile oils, nonvolatile oil complexes, fatty alcohols and fatty acid esters meet the above requirements. The nonvolatile oils and oil complexes comprise a large groups of chemical compositions which are insoluble in water and in general have the desired characteristics discussed above.

The non-volatile oils and oil complexes include oils derived from petroleum (aliphatic), plants (vegetable) and animals. For example, the following oils have been used with the dispensing pad of the invention and provided a significant increase in the image contrast of a fingerprint captured by a live-scan-fingerprint reader:

mink oil, conventional 10–30 motor oil, corn oil vaseline petroleum jelly, corn oil margarine, WD-40, mineral oil, silicone oil, cod liver oil, olive oil, almond oil, glyceryl monooleate, oleic acid, and diethanolamides (DEA's), namely coco diethanolamide and soya diethanolamide.

It should be noted that fixed or fatty oils may be partially hydrogenated to increase their viscosity as long the end product is dispensible in the dispensing pad of this invention.

The fatty alcohols include behenyl, iso-stearlyl, iso-cetyl, arachidyl, stearyl, cetyl, oleyl, myristyl, lauryl, decyl and octyl. The fatty acid esters include the reaction products of one or more of the alcohols and one or more of the fatty acids identified in the table below:

|  | ALCOHOL TYPE | FATTY ACID |
| --- | --- | --- |
| PRIMARY | methyl | myristic |
|  | ethyl | oleic |
|  | propyl | lauric |
|  | butyl | stearic |
|  | isopropyl | palmitic |
| DIOLS | glycols |  |
| TRIOL | glycerol |  |

To aid in transferring these chemicals to the skin, they may be used in connection with a suitable wetting agent. Amphoteric surfactants are very effective for this purpose since these surfactants attract both oil and water, and tolerate both acidic and alkaline environments. Skin pH varies according to a person's biochemistry. The preferred embodiment of a liquid in accordance with the invention is a mixture of isopropyl myristate, anhydrous lanolin, and cocamidopropyl betaine.

The following pad materials and formulations for the liquid composition are given by way of example only and are not to be considered as limiting the scope of the invention.

EXAMPLE 1

A fingerprint pad was constructed by mechanically coupling high-density felt to medium weight blotter paper (e.g., having a thickness in the range of 0.010" to 0.020") such that the felt served as a reservoir and the blotter served as a metering surface. Both materials were impregnated with silicone oil (dimethylpolysiloxane). The pad was used to coat the thumb with the oil and comparisons were made between images produced by a live-scan-fingerprint reader both before and after the treatment. A very significant increase of image contrast was created by the oil coating. However, the blotter paper does not provide the same accurate metering as the ceramic or plastic metering substrates discussed above. As a result a slightly excessive amount of residue was deposited upon the optical window using the felt blotter paper applicator.

EXAMPLE 2

An open-cell polyvinyl chloride foam, having a pore volume of 60 to 63 percent and a thickness of 0.40 inches, was compressed slightly with heat and pressure slightly to make its surface exceptionally smooth. The foam was die-cut to the size of a typical fingerprint pad, then impregnated with a mixture of 99 parts glycerol monoricinoleate and 1 part Dowfax® 2A-2 surfactant. The results were substantially identical to those achieved with Example 1. Dowfax® is a trademark of the Dow Chemical Company.

EXAMPLE 3

A rectangular fingerprint pad composed of two kinds of high-density polyethylene plastic was molded to provide a reservoir pad with a pore size of 35 to 40 microns and a pore volume of 40 to 45 percent, and a metering top pad with a pore size of 4 to 7 microns and a pore volume of 18 to 22 percent. The pad was impregnated with a mixture of 98 parts diethylene glycol monolaurate and 2 parts polysorbate 80. The results were similar to those achieved with Example 1, i.e., a high degree of image enhancement and clarity except that very little residue left on the optical window.

EXAMPLE 4 (Preferred Embodiment)

The liquid composition was prepared by dissolving 100 grams of anhydrous lanolin in 1000 milliliters of isopropyl myristate mixed with 20 milliliters of cocamidopropyl betaine. A medium density, fully reticulated, polyester foam layer was bonded to a microporous ceramic disk having a mean pore size of 0.93 microns and having a pore volume of 41 percent (as in FIG. 5) to create a reservoir and a substantially rigid, porous metering surface. The pad was impregnated with the liquid composition. This pad/composition arrangement was tested in the same manner as in Example 1. The result was that very dark and exceptionally clear fingerprints were produced with virtually no residue left on the optical window.

EXAMPLE 5

A one ounce per square yard of melt-blown polyester fabric was trimmed to form a pad of 1.25 inches by 2 inches. The pad was then affixed to a polyethylene-coated-foil film using heat and pressure. 0.15 millimeters of the liquid composition of Example 4 was injected into the pad. The laminate was then folded and sealed to form a hermetically sealed package similar to a towelette. The package was then unsealed and tested. The results were like those of Example 1. It should be noted that fatty acids such as oleic acid provide excellent results when maintained in a sealed package prior to use. Such fatty acids tend to rapidly oxidize and become rancid when exposed to air and thus have a short shelf life in the absence of the use of such sealed packages.

EXAMPLE 6

A 3 inch by 5 inch by 0.025 inch piece of microcellular PTFE (trade name Teflon®) was impregnated under vacuum with the liquid composition of Example 4. The material was blotted between layers of paper towel to remove most of the liquid. The test and results were like those of Example 1. Teflon® is a trademark of Dow Chemical Company.

While the invention has been described in connection with a preferred embodiment, it is not intended that the scope of the invention be limited to the particular embodiments and examples discussed above. Various alternatives, modifications, and equivalents will become apparent to those skilled in the art without departing from the spirit and scope of the invention as defined by the appended claims.

What is claimed is:

1. A combination dispensing pad and chemical reagent for applying a chemical composition to the fingerprint area of a person's fingers prior to the placement thereof on the imaging platen of a live-scan-electro-optical-fingerprint-imaging apparatus to provide a clear optical boundary between the ridges defining the person's fingerprint and the surface of the platen comprising:

a substantially noncompressible microporous pad formed from a ceramic or polyethylene material and having a pore volume within the range of about 10 to 50% and a pore diameter within the range of about 0.1 to 10 microns; and a liquid chemical composition disposed within the pad, the composition consisting of one or more materials selected from the group of nonvolatile oils, nonvolatile oil complexes, fatty alcohols and fatty acid esters.

2. The dispensing pad and chemical reagent of claim 1 wherein the absorbent pad includes a microporous pad having a top surface through which the chemical composition is supplied to the fingerprint area of the person's finger, the pad further having a pore volume within the range of about 10 to 50 percent and a mean pore diameter within the range of about 0.10 to 10.0 microns, the pad being substantially noncompressible in response to the pressure of a fingertip placed thereon for coating purposes.

3. The dispensing pad and chemical reagent of claim 2 wherein the absorbent pad further includes a reservoir positioned below the microporous pad.

4. The dispensing pad and chemical reagent of claim 3 wherein the microporous pad is made of ceramic with a mean pore diameter within the range of 0.90 to 1.0 microns.

5. The dispensing pad and chemical reagent of claim 1 wherein the microporous pad is made of polyethylene.

6. The dispensing pad and chemical reagent of claim 1 wherein the chemical composition consists of materials selected from the group of nonvolatile oils and nonvolatile oil complexes.

7. The dispensing pad and chemical reagent of claim 6 wherein the nonvolatile oil complexes are diethanolamides.

8. The dispensing pad and chemical reagent of claim 7 wherein the nonvolatile oil complexes are chosen from group consisting of coco diethanolamide and soya diethanolamide.

9. The dispensing pad and chemical reagent of claim 1 wherein the chemical composition consists of one or more fatty alcohols selected from the group of behenyl, iso-stearlyl, iso-cetyl, arachidyl, stearyl, cetyl, oleyl, myristyl, lauryl, decyl, and octyl.

10. The dispensing pad and chemical reagent of claim 1 wherein the chemical composition consists of one or more fatty acid esters formed by the reaction products of one or more of the following alcohols methyl, ethyl, propyl, butyl, isopoply, glycols, glycerol and polyol with one or more of the following fatty acids myristic, oleic, lauric, stearic, and palmitic.

11. The dispensing pad and chemical reagent of claim 10 wherein the fatty acid ester of alcohol is isopropyl myristrate.

* * * * *